United States Patent [19]

Leblanc et al.

[11] Patent Number: 5,026,926
[45] Date of Patent: Jun. 25, 1991

[54] CHLORINATION OF ORTHO-CHLOROPHENOL

[75] Inventors: Jean-Claude Leblanc, Grenoble; Serge Ratton, Villefontaine; Bernard Besson, Pont de Claix; Jean-Roger Desmurs, Saint-Symphorien d'Ozon, all of France

[73] Assignee: Rhone-Poulenc Chimie, Courbevoie, France

[21] Appl. No.: 164,966

[22] Filed: Mar. 7, 1988

[30] Foreign Application Priority Data

Mar. 5, 1987 [FR] France ............... 87 03207

[51] Int. Cl.$^5$ ............... C07C 37/62; C07C 39/32
[52] U.S. Cl. ............... 568/779; 568/774; 568/776
[58] Field of Search ............... 568/774, 776, 779

[56] References Cited

U.S. PATENT DOCUMENTS

| | | | |
|---|---|---|---|
| 2,659,759 | 11/1953 | Zemba | 568/779 |
| 4,237,321 | 12/1980 | Cuthbertson | 568/779 |
| 4,827,047 | 5/1989 | Desmurs et al. | 568/779 |
| 4,855,513 | 8/1989 | Besson et al. | 568/779 |
| 4,876,396 | 10/1989 | Leblanc et al. | 568/779 |

FOREIGN PATENT DOCUMENTS

| | | | |
|---|---|---|---|
| 0196260 | 10/1986 | European Pat. Off. | 568/779 |
| 0216714 | 4/1987 | European Pat. Off. | 568/776 |
| 0283411 | 9/1988 | European Pat. Off. | 568/776 |
| 0299892 | 1/1989 | European Pat. Off. | 568/776 |
| 1046061 | 12/1958 | Fed. Rep. of Germany | 568/779 |
| 3318791 | 12/1983 | Fed. Rep. of Germany | 568/779 |
| 2587332 | 3/1987 | France | 568/779 |
| 0220302 | 3/1985 | German Democratic Rep. | 568/779 |
| 573477 | 5/1950 | United Kingdom | 568/779 |

*Primary Examiner*—Werren B. Lone
*Attorney, Agent, or Firm*—Burns, Doane, Swecker & Mathis

[57] ABSTRACT

The polychlorophenols, e.g., 2,6-dichlorophenol (a known agrochemical intermediate), are effectively prepared by chlorinating ortho-chlorophenol with gaseous chlorine, optionally in the presence of other chlorophenols, characteristically in the molten state, and in the presence of a catalytically effective amount of a primary, secondary or tertiary amine.

19 Claims, No Drawings

CHLORINATION OF ORTHO-CHLOROPHENOL

CROSS-REFERENCE TO COMPANION APPLICATION

Copending applications, Ser. No. 164,894 and Ser. No. 165,007, both filed concurrently herewith and both assigned to the assignee hereof.

BACKGROUND OF THE INVENTION

1. Field of the Invention

The present invention relates to the chlorination of ortho-chlorophenol and, more especially, to the chlorination of ortho-chlorophenol to produce 2,6-dichlorophenol.

2. Description of the Prior Art

Published German Patent Application No. 3,318,791 describes a process for the selective chlorination of phenol to ortho-chlorophenol, in a perchlorinated non-polar solvent medium and in the presence of a branched-chain amine.

Published French Patent Application No. 85/03,802 describes the selective chlorination of various compounds, including ortho-chlorophenol, at the ortho position with respect to the phenol group, in an a polar aprotic solvent medium and in the presence of a primary, secondary or tertiary amine.

This process is very selective, but it entails the use of a solvent, thereby complicating the subsequent treatment parameters.

SUMMARY OF THE INVENTION

Accordingly, a major object of the present invention is the provision of an improved process for the chlorination of ortho-chlorophenol with gaseous chlorine into 2,6-dichlorophenol, which improved process is conspicuously devoid of the solvent media to date characterizing the state of the art.

Briefly, the present invention features the chlorination of ortho-chlorophenol with gaseous chlorine into 2,6-dichlorophenol, wherein the reaction is carried out in the molten state and in the presence of a catalytically effective amount of at least one primary, secondary or tertiary amine.

DETAILED DESCRIPTION OF THE PREFERRED EMBODIMENTS OF THE INVENTION

More particularly according to the present invention, by the term "amine" is intended any organic nitrogen compound that is liquid or solid under the working conditions of the subject process and contains one or more amine groups.

Such a compound can also contain one or more other functional groups such as, for example, the hydroxyl group, the carboxylic acid group, the carboxylic acid ester group, the amide group or the imine group.

It will of course be appreciated that the amines used can also be introduced in the form of their salts, and more especially their respective hydrochlorides.

The term "amine" also encompasses ammonia as well as the salts, and, in particular, the amine hydrochlorides.

The amines which serve as a catalyst in the subject process are more preferably the amines having the general formula (I):

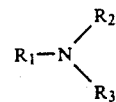

in which
$R_1$, $R_2$ and $R_3$, which may be identical or different, are each a linear alkyl radical having from 1 to 12 carbon atoms, a secondary alkyl radical having from 3 to 12 carbon atoms or a tertiary alkyl radical having from 4 to 12 carbon atoms, with the proviso that such alkyl radicals may contain one or two —O— ether groups or hydroxyl, amine, carboxylic acid, carboxylic acid ester, amide or imine groups; a phenyl radical, a cyclohexyl radical, a cycloheptyl radical or a cyclopentyl radical; a phenylalkyl, cyclohexylalkyl, cycloheptylalkyl or cyclopentylalkyl radical, the alkyl moiety of which contains from 1 to 4 carbon atoms; or a hydrogen atom; with the further provisos that:

$R_1$ may be an $NH_2$ group;

$R_2$ and $R_3$ may from, together with the nitrogen atom from which they depend, a saturated heterocycle or a heterocycle containing one or more double bonds, optionally substituted with one or more alkyl groups having from 1 to 4 carbon atoms;

$R_2$ and $R_3$ or $R_1$, $R_2$ and $R_3$ may form, together with the nitrogen atom from which they depend and with one or more other nitrogen and/or oxygen and/or sulfur atoms, a saturated or unsaturated heterocycle optionally substituted with one or more alkyl groups having from 1 to 4 carbon atoms;

$R_1$, $R_2$ and $R_3$ may form, together and with the nitrogen atom from which they depend, an unsaturated heterocycle optionally substituted with one or two methyl or ethyl groups;

$R_2$ and $R_3$ or $R_1$, $R_2$ and $R_3$ may form, together with the nitrogen atom from which they depend and optionally with one or more other nitrogen and/or oxygen and/or sulfur atoms, a saturated or unsaturated polycyclic compound optionally substituted with one or more alkyl groups having 1 to 4 carbon atoms.

Exemplary of such amines of formula (I), the following are representative:

(i) ammonia;

(ii) primary amines such as n-propylamine, isopropylamine, isobutylamine, n-butylamine, tertbutylamine, n-pentylamine, 2-methylbutylamine, 3-methylbutylamine, n-hexylamine, 2-ethylhexylamine, aniline, laurylamine, cyclohexylamine, cyclopentylamine, benzylamine, guanidine, acetamidine, glycine ether ester, ethanolamine, ethylenediamine, hexamethylenediamine, N-aminoethylpyrrolidine, pyrazoline, lysine, n-aminomorpholine and N-aminopiperidine;

(iii) secondary amines such as dibutylamine, dipropylamine, methylpropylamine, methylbutylamine, methylisobutylamine, methyl-tert-butylamine, methylbenzylamine, di-tert-butylamine, 1-methylcyclopentylamine, 1-methylcyclohexylamine, dicyclohexylamine, morpholine, imidazole, pyrrolidine, imidazolidine, piperazine and indole;

(iv) tertiary amines such as triethylamine, tributylamine, pyridine, tris(3,6-dioxaheptyl) amine and 1,8-diazabicyclo[5.4.0]undec-7-ene.

It is also possible to use amino compounds such as hydrazine or its derivatives, in particular the derivatives obtained by substitution of one or two hydrogen atoms with alkyl, aryl, cycloaliphatic or heterocyclic radicals.

The quantity of the amine used in the process can vary over very wide limits.

It usually represents from 0.005% to 10% by weight relative to the weight of the reaction medium. preferably, from 0.015% to 5% by weight of amine relative to the reaction medium will be employed, in order to have sufficient efficacy, while not having an excessive amount of the amine.

Among the amines of the general formula (I), more preferred are the primary or secondary amines of the formula (II):

in which

R$_2$ or R$_3$ may be a hydrogen atom; and R$_2$ and R$_3$, which may be identical or different, are each a linear alkyl radical having from 1 to 10 carbon atoms; a secondary alkyl radical having from 3 to 10 carbon atoms; a tertiary alkyl radical having from 4 to 10 carbon atoms; a cyclohexyl or cyclopentyl radical; a phenyl radical; or a benzyl or phenethyl radical; with the provisos that:

R$_2$ and R$_3$ may form, together with the nitrogen atom from which they depend and with another nitrogen and/or oxygen atom, a saturated heterocycle or a heterocycle containing one or more unsaturated bonds; and R$_2$ and/or R$_3$ may contain one or more amine, hydroxyl or carboxylic acid ester groups.

As specific examples of primary amines of the general formula (II), representative are n-propylamine, isopropylamine, n-butylamine, isobutylamine, tertbutylamine, n-pentylamine, 2-methylpentylamine, 3-methylpentylamine, 2-ethylhexylamine, laurylamine, cyclohexylamine, cyclopentylamine, benzylamine, glycine ethyl ester and ethanolamine.

As regards, more especially, the secondary amines of general formula (II), more preferred are those in which at least one of the symbols R$_2$ and R$_3$, and preferably both symbols R$_2$ and R$_3$, are a secondary alkyl radical having from 3 to 10 carbon atoms, such as isopropyl, 2-butyl, 2-pentyl, 3-pentyl, 2-hexyl, 3-hexyl, 2-heptyl, 3-heptyl, 4-heptyl, 2-octyl, 3-octyl, 4-octyl, 2-nonyl, 3-nonyl, 4-nonyl, 5-nonyl, 2-decyl, 3-decyl, 4-decyl and 5-decyl; a cyclohexyl or cyclopentyl radical; and those in which R$_2$ and R$_3$ form, together with the nitrogen atom from which they depend, a heterocycle optionally containing another nitrogen atom or an oxygen atom.

As specific examples of such secondary amines, diisopropylamine, diisobutylamine, dicyclohexylamine, morpholine and imidazole are representative.

A very advantageous embodiment of the process of the invention entails carrying out the chlorination of the ortho-chlorophenol diluted in at least one polychlorophenol.

More specifically, this preferred embodiment features a process for the chlorination of ortho-chlorophenol with gaseous chlorine into 2,6-dichlorophenol, wherein the reaction is carried out in the molten state in the presence of:

(a) at least one polychlorophenol in such amount that the ratio by weight ortho-chlorophenol/total chlorophenols is less than or equal to 30%; and (b) a catalytically effective amount of at least one primary, secondary or tertiary amine.

Usually, as in the general chlorination process, the amine constitutes from 0.005% to 10% by weight relative to the weight of the reaction medium.

Preferably, as indicated above, from 0.015% to 5% by weight of amine relative to the weight of the reaction medium is used.

The amines (or their hydrochlorides) are those which have been defined above.

The polychlorophenols, in the presence of which this embodiment of the process of the invention is carried out, are principally 2,4-dichlorophenol, 2,6-dichlorophenol and 2,4,6-trichlorophenol. There can also be other polychlorophenols in the reaction mixture, such as 2,3,4,6-tetrachloro- or pentachlorophenol. The chlorination of ortho-chlorophenol alone in the molten state with gaseous chlorine results in a preponderance of 2,6-dichlorophenol.

The preferred embodiment of the chlorination of ortho-chlorophenol in the molten state, diluted with polychlorophenols, attains a still greater selectivity for the chlorination to 2,6-dichlorophenol compared with chlorination to 2,4-dichlorophenol.

In general, by means of this embodiment of the invention, it is possible to obtain a selectivity equal to or greater than 0.70 mole of 2,6-dichlorophenol formed per 1 mole of ortho-chloropheno introduced.

The 2,4-dichlorophenol which is formed in a smaller proportion is converted for the most part into 2,4,6-trichlorophenol.

The temperature at which the process according to the invention is carried out generally ranges from the melting point of ortho-chlorophenol and of the polychlorophenols which may be present to 150° C. In practice, this temperature ranges from 65° C. to 120° C., but these values are not critical.

The flow rate of chlorine injected depends both on the apparatus and on the concentration of amine and orthochlorophenol in the reaction medium.

As a general rule, the higher the amine concentration, especially relative to the orthochlorophenol present, the larger can be the flow rate. Similarly, a higher concentration of ortho-chlorophenol in the medium permits a larger flow rate of chlorine.

The presence of the amine permits a good binding of chlorine to be achieved. Thus, it is generally unnecessary to introduce an excess of chlorine relative to the stoichiometric quantity.

The problems of recycling the excess chlorine or of treating the gaseous effluents thus become less difficult to remedy.

The chlorine can be used alone or can be diluted with an inert gas such as nitrogen, for example. The presence of an inert gas enables, if necessary, the gaseous flow rate to be increased without increasing the quantity of chlorine introduced in a given period of time.

The process of the invention can be carried out in continuous or discontinuous fashion.

It is very advantageous to apply the present process to a mixture of ortho-chlorophenol and 2,4,6-trichlorophenol. Most of the ortho-chlorophenol is converted into 2,6-dichlorophenol, while another fraction is converted to 2,4-dichlorophenol which is itself chlorinated to 2,4,6-trichlorophenol. At the end of the chlorination, a mixture of 2,6-dichlorophenol and 2,4,6-trichlorophenol is hence obtained, these two compounds being especially useful intermediates in the synthesis of crop chemicals.

Another embodiment of the process of the invention entails first chlorinating the ortho-chlorophenol in the molten state in the presence of an amine as described above. This chlorination gives a preponderance of 2,6-dichlorophenol, as well as 2,4-dichlorophenol and 2,4,6-trichlorophenol.

When the concentration of ortho-chlorophenol in the reaction medium reaches a value less than or equal to approximately 30% by weight, ortho-chlorophenol is injected therein in continuous fashion simultaneously with the injection of gaseous chlorine.

The flow rates are such that the concentration by weight of ortho-chlorophenol in the reaction medium is always less than or equal to 30%. Thus, the orthochlorophenol injected is converted very preponderantly into 2,6-dichlorophenol.

When desired, the addition of ortho-chlorophenol is stopped and the chlorination is continued until the ortho-chlorophenol present in the reaction medium has completely disappeared.

At the end of the reaction, a mixture of 2,6-dichlorophenol and 2,4,6-trichlorophenol is thereby obtained.

The richness of this mixture with respect to 2,6-dichlorophenol will be in proportion to the quantity of ortho-chlorophenol injected during the second stage of the chlorination.

Finally, another embodiment of the process of the invention comprises preparing 2,4,6-trichlorophenol from 2,6-dichlorophenol or, where appropriate, from the mixture of 2,6-dichlorophenol and 2,4,6-trichlorophenol obtained consistent herewith.

This embodiment comprises introducing an effective amount of strong acid or Lewis acid into the reaction medium containing 2,6-dichlorophenol mixed, where appropriate, with 2,4,6-trichlorophenol.

By "strong acid" is intended a protonic acid having an acidity function Ho of less than or equal to $-5$.

Exemplary of such strong acids, sulfuric acid, perchloric acid, trifluoromethanesulfonic acid, chlorosulfonic acid, fluorosulfonic acid, fuming sulfuric acid and acidic resins containing fluorosulfonic groups are representative.

By "Lewis acid" is intended its usual definition, compounds that are electron-pair acceptors. It is possible to use, in particular, the Lewis acids mentioned in the text edited by G.A. Olah, *Friedel-Crafts and Related Reactions,* volume I, pages 191 to 197 (1963).

The Lewis acids preferably used in this embodiment of the process are, more especially, the halides of the elements of Groups 3a, 4a, 5a, 1b, 2b, 4b, 5b, 6b, 7b, and 8 of the Periodic Table, which are liquid or solid under the working conditions of the reaction such as aluminum, tin, phosphorus, antimony, arsenic, bismuth, titanium, tantalum, niobium, zirconium, vanadium, tungsten, molybdenum, iron, cobalt, nickel, copper, zinc and calcium chlorides, bromides, fluorides and iodides.

As specific examples of such halides, aluminum chloride, aluminum bromide, stannic and stannous chlorides, stannic and stannous bromides, bismuth trichloride, titanium tetrachloride, zirconium tetrachloride, antimony pentafluoride, tungsten hexachloride, the molybdenum chlorides, ferric chloride, ferrous chloride, ferric bromide, ferrous bromide, cuprous chloride, cupric chloride and zinc chloride are representative.

Among these Lewis acids, aluminum chloride, ferric chloride, zirconium tetrachloride and titanium tetrachloride are preferred.

It is also possible to use complexes of certain Lewis acids with a hydracid, to the extent that these complexes are liquid or solid under the reaction conditions. Thus, for example, the complex $SbF_5 \cdot HF$ is representative.

In general, the amount of strong acid or Lewis acid used in such that the ratio by weight strong acid/2,6-dichlorophenol or Lewis acid/2,6-dichlorophenol ranges from 0.01% to 10%.

Preferably, these ratios by weight range from 0.1% 25 to 5%.

Since in the subject process the reactants are in the molten state, the use of a strong protonic acid is more especially preferred.

Thus, 2,4,6-trichlorophenol generally containing less than 3% by weight of 2,4,5,6,6-pentachloro-2-cyclohexenone is obtained in excellent yield.

In order to further illustrate the present invention and the advantages thereof, the following specific examples are given, it being understood that same are intended only as illustrative and in nowise limitative

EXAMPLE 1

A 500-cm$^3$ glass reactor equipped with a dipping tube provided with a sintered glass end, a thermometer pocket and a water-cooled reflux condenser was charged with:

(i) 35.5 g of ortho-chlorophenol (0.276 mol): 14.2 mol %;

(ii) 330 g of 2,4,6-trichlorophenol (1.662 mol): 85.8 mol %;

(iii) 0.4 g of dibutylamine (approximately 0.1% by weight relative to the reaction mixture)

The mixture was heated to approximately 70° C. using a thermostatic bath, before gaseous chlorine was introduced via the dipping tube at a flow rate of 20 liters/hour. The temperature was maintained at between 65° C. and 75° C. during the chlorination.

After 6 minutes of chlorination, the molar composition of the reaction mass was analyzed by gas chromatography.

The following results were found:
ortho-chlorophenol: 6.45%
2,6-dichlorophenol: 5.8 %
2,4-dichlorophenol: 1.75%
2,4,6-trichlorophenol: 86.0 %

This showed that the selectivity of the chlorination of ortho-chlorophenol to 2,6-dichlorophenol was 0.75 mol/mol.

The chlorination was continued for 12 minutes until the ortho-chlorophenol and 2,4-dichlorophenol had almost completely disappeared (less than 0.2% in the mixture).

The following mixture was obtained (mol % determined by gas chromatography):
2,6-dichlorophenol: 10.4%
2,4,6-trichlorophenol: 89.6%

The selectivity was 0.73 mol of 2,6-dichlorophenol mol of ortho-chlorophenol introduced.

EXAMPLE 2

Example 1 was repeated with the following charges:
(i) 55 g of ortho-chlorophenol (0.428 mol): 27.8 mol %;
(ii) 220 g of 2,4,6-trichlorophenol (1.108 mol); 72.2 mol %;

(ii) 0.28 g of diisopropylamine (0.1% by weight relative to the reaction mixture).

Chlorination was carried out under the conditions of Example 1, such as to convert all the ortho-chlorophenol as well as the 2,4-dichlorophenol formed.

The following final mixture was obtained (mol % determined by gas chromatography):
2,6-dichlorophenol: 20.9%
2,4,6-trichlorophenol: 79.1%

This corresponds to a selectivity of 0.75 mol of 2,6-dichlorophenol formed per 1 mol of ortho-chlorophenol introduced.

EXAMPLE 3

The apparatus described in Example 1 was charged with: (i) 240 g of ortho-chlorophenol (1.712 mol);
(ii) 2.4 g of dibutylamine (1.0% by weight relative to ortho-chlorophenol).

The mixture was heated to 70° C. and gaseous chlorine was then introduced via the dipping tube at a flow rate of approximately 40 liters/hour until the molar concentration of ortho-chlorophenol was less than 10% (progress monitored by gas chromatography).

Thus, after chlorination for approximately one hour, the reaction mixture had the following molar composition:
ortho-chlorophenol: 6.8%
2,6-dichlorophenol: 50.9%
2,4-dichlorophenol: 39.4%
2,4,6-trichlorophenol: 2.9%

The selectivity of the reaction at this stage was 0.55 mol of 2,6-dichlorophenol formed per one mol of ortho-chlorophenol introduced.

This mixture was transferred to a 1-liter glass reactor, equipped as above but containing in addition an injection tube for ortho-chlorophenol.

While the temperature was maintained at 70°–75° C., the following were injected simultaneously into the reactor:
240 g/hour of ortho-chlorophenol
chlorine at a flow rate of 45 liters/hour.

Monitoring by chromatographic analysis showed that the concentration of ortho-chlorophenol remained less than 10% by weight in the medium (it varied between 3% and 8% by weight during the experiment).

After 8 hours of chlorination, a reaction mixture having the following molar composition was obtained:
ortho-chlorophenol: 3.7%
2,6-dichlorophenol: 65.0%
2,4-dichlorophenol: 10.4%
2,4,6-trichlorophenol: 20.9%

The addition of ortho-chlorophenol was then stopped and the chlorination was continued until the orthochlorophenol present and the 2,4,-dichlorophenol had completely disappeared.

The final reaction mixture had the following molar composition:
2,6-dichlorophenol: 66.0%
2,4,6-trichlorophenol: 34.0%

EXAMPLE 4

Example 3 was repeated, using diisopropylamine as a chlorination catalyst.

The following were first charged:
(i) 235 g of ortho-chlorophenol,
(ii) 2.4 g of diisopropylamine.

The mixture was heated to about 70° C. and gaseous chlorine was then introduced via the dipping tube at a flow rate of approximately 40 liters/hour for 1 hr, 20 min.

The molar composition of the reaction mixture was then as follows:
ortho-chlorophenol: 0.5%
2,6-dichlorophenol: 60.3%
4-dichlorophenol: 38.1% 2,4,6-trichlorophenol: 1.1%

The selectivity at this stage was 0.60 mol of 2,6-dichlorophenol formed per 1 mol of ortho-chlorophenol introduced.

The procedure was then as described in Example 5: in the second reactor, the following were injected simultaneously for 8 hours:
240 g/hour of ortho-chlorophenol;
approximately 45 liters/hour of gaseous chlorine.

Monitoring by chromatographic analysis showed that the concentration of ortho-chlorophenol remained less than 10% by weight in the medium.

After 8 hours of chlorination, the reaction mixture had the following molar composition:
ortho-chlorophenol: 2.7%
2,6-dichlorophenol: 65.4%
2,4-dichlorophenol: 8.4%
2,4,6-trichlorophenol: 23.5%

The addition of ortho-chlorophenol was then stopped and the chlorination was continued until the orthochlorophenol present and the 2,4-dichlorophenol had completely disappeared.

The final reaction mixture had the following molar composition:
2,6-dichlorophenol: 70.0%
2,4,6-trichlorophenol: 30.0%

EXAMPLE 5

A 500-cm$^3$ glass reactor equipped as described in Example 1 was charged with:
(i) 35.5 g of ortho-chlorophenol (0.276 mol): 14.2 mol %;
(ii) 330 g of 2,4,6-trichlorophenol (1.662 mol): 85.8 mol %;
(iii) 0.4 g of dibutylamine (0.0031 mol) (0.11% by weight relative to the reaction medium).

The mixture was heated to 70° C. and gaseous chlorine was introduced via the dipping tube at a flow rate of 15 liters/hour.

The temperature was maintained at approximately 70° C. and the progress of the reaction was monitored by analysis of samples withdrawn at intervals of time.

After 14 minutes, all the ortho-chlorophenol had been converted.

The reaction mass had the following molar composition, determined by gas chromatography:
ortho-chlorophenol: <0.1%
2,6-dichlorophenol: 11.8%
2,4-dichlorophenol: 1.3%
2,4,6-trichlorophenol: 86.9%

The selectivity of the chlorination of orthochlorophenol to 2,6-dichlorophenol was 0.83 mol/mol.

COMPARATIVE EXPERIMENT A

By way of comparison, Example 5 was repeated without the inclusion of an amine.

The chlorination conditions were the same as in Example 5, but the time needed for conversion of all the ortho-chlorophenol was 17 minutes.

The molar composition of the final reaction mixture was as follows:
ortho-chlorophenol: <0.1%

2,6-dichlorophenol: 4.3%
2,4-dichlorophenol: 8.9%
2,4,6-trichlorophenol: 86.8%

The selectivity of the chlorination of orthochlorophenol to 2,6-dichlorophenol was 0.30 mol/mol.

EXAMPLE 6

The procedure was as in Example 5, but with a reduction in the ratio by weight amine/reaction medium. The following were charged:
(i) 27.0 g of ortho-chlorophenol (0.21 mol);
(ii) 230 g of 2,4,6-trichlorophenol (1.165 mol);
(iii) 0.130 g of dibutylamine (0.001 mol): 0.05% by weight of amine/reaction medium.

The chlorination conditions were identical to those of Example 5.

After 17 minutes, all the ortho-chlorophenol had been converted.

The molar composition of the final reaction medium was as follows:
ortho-chlorophenol: <0.1%
2,6-dichlorophenol: 11.2%
2,4-dichlorophenol: 3.0%
2,4,6-trichlorophenol: 85.8%

The selectivity was 0.73 mol of 2,6-dichlorophenol formed per 1 mol of ortho-chlorophenol introduced.

COMPARATIVE EXPERIMENT B

A 100-cm$^3$ glass reactor equipped as in Example 1 was charged with 38.6 g (0.3 mol) of ortho-chlorophenol.

The ortho-chlorophenol was heated to 50° C. and 0.27 mol of chlorine was then introduced at this temperature at a flow rate of 5 1/hr.

When the addition of chlorine was complete, the reactor was purged with nitrogen. The reaction mixture (48.14 g) was analyzed by gas chromatography. The molar composition was as follows:
ortho-chlorophenol: 11.5%
6-dichlorophenol: 20.8%
2,4-dichlorophenol: 66.3%
2,4,6-trichlorophenol: 1.5%

The selectivity of the chlorination of orthochlorophenol to 2,6-dichlorophenol was 0.24 mol/mol.

EXAMPLE 7

The procedure was as in Example 5, with the following charges:
(i) 55.0 g of ortho-chlorophenol (0.428 mol);
(ii) 220 g of 2,4,6-trichlorophenol (1.108 mol);
(iii) 0.275 g of dibutylamine (0.0021 mol).

The chlorination conditions were the same as in Example 5.

After 34 minutes, all the ortho-chlorophenol had been converted.

The molar composition of the final reaction mixture was as follows:
orthochlorophenol: 0%
2,6-dichlorophenol: 22.4%
2,4-dichlorophenol: 2.1%
2,4,6-trichlorophenol: 75.5%.

The selectivity was 0.81 mol of 2,6-dichlorophenol formed per 1 mol of ortho-chlorophenol introduced.

EXAMPLE 8

The procedure was as in Example 5, with the following charges:
(i) 100 g of ortho-chlorophenol (0.778 mol);
(ii) 150 g of 2,4,6-trichlorophenol (0.754 mol);
(iii) 0.250 g of dibutylamine (0.0019 mol).

The flow rate of chlorine was 30 liters/hour and the temperature was approximately 70° C.

After 43 minutes, all the ortho-chlorophenol had been converted.

The molar composition of the final reaction mixture was as follows:
orthochlorophenol: <0.1%
2,6-dichlorophenol: 31.1%
2,4-dichlorophenol: 17.7%
2,4,6-trichlorophenol: 55.3%

The selectivity was 0.62 mol of 2,6-dichlorophenol per 1 mol of ortho-chlorophenol introduced.

EXAMPLE 9

The procedure was as in Example 5, with the following charges:
(i) 240 g of ortho-chlorophenol (1.867 mol);
(ii) 7.0 g of dibutylamine (2.9% by weight relative to the ortho-chlorophenol).

The flow rate of chlorine was 30 liters/hour and the temperature was approximately 70° C.

After 71 minutes of reaction, the molar composition of the reaction mixture was as follows:
ortho-chlorophenol: 1.9%
2,6-dichlorophenol: 49.3%
2,4-dichlorophenol: 44.2%
2,4,6-trichlorophenol: 4.6%

The selectivity was 0.51 mol of 2,6-dichlorophenol per 1 mol of ortho-chlorophenol introduced.

EXAMPLE 10

A 200-cm$^3$ glass reactor equipped as described in Example 1 was charged with:
(i) ortho-chlorophenol: 9.0 g (70 mmol);
(ii) 2,6-dichlorophenol: 51 g (312.9 mmol);
(iii) diisopropylamine: 0.06 g.

The reaction mixture was heated to 70° C. under stirring and gaseous chlorine was introduced at a flow rate of 5 1/hour for 18 min, 50 s, which represented a quantity of chlorine introduced of 70 mmol.

The reaction mixture was analyzed by GC and HPLC.

The following results were obtained:
DC of ortho-chlorophenol: 94.0%
YLD of 2,6-dichlorophenol: 64.3%
YLD of 2,4-dichlorophenol: 22.5%
YLD of 2,4,6-trichlorophenol: 6.7%

0.3 of trifluoromethanesulfonic acid (0.5% by weight) was then introduced, after which gaseous chlorine was again introduced at a flow rate of 5 1/hr for 2 hours, which represented a quantity of chlorine introduced of 446 mmol.

After the reactor was purged with nitrogen, the final reaction mixture was analyzed by GC and HPLC. The following results were obtained:
DC of ortho-chlorophenol and 2,6-dichlorophenol: 98.8%
YLD of 2,4,6-trichlorophenol relative to the ortho-chlorophenol and 2,6-dichlorophenol converted: 97.5%
YLD of pentachlorocyclohexenone: 2.7%

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a polychlorophenol, comprising reacting ortho-chlorophenol with gaseous chlorine, in a solvent-free reaction medium, in the presence of a catalytically effective amount of a primary, secondary or tertiary amine.

2. The process as defined by claim 1, comprising carrying out the reaction in the molten state.

3. The process as defined by claim 2, said amine catalyst having the general formula (I):

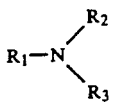

in which
$R_1$, $R_2$ and $R_3$, which may be identical or different, are each a linear alkyl radical having from 1 to 12 carbon atoms, a secondary alkyl radical having from 3 to 12 carbon atoms or a tertiary alkyl radical having from 4 to 12 carbon atoms, with the proviso that such alkyl radicals may contain one or two —O— ether groups or hydroxyl, amine, carboxylic acid, carboxylic acid ester, amide or imine groups; a phenyl radical, a cyclohexyl radical, a cycloheptyl radical or a cylcopentyl radical; a phenylalkyl, cyclohexylalkyl, cycloheptylalkyl or cyclopentylalkyl radical, the alkyl moiety of which contains from 1 to 4 carbon atoms; or a hydrogen atom; with the further provisos that:

$R_1$ may be an $NH_2$ group;

$R_2$ and $R_3$ may from, together with the nitrogen atom from which they depend a saturated heterocycle, a heterocycle containing one or more double bonds, or a heterocycle containing one or more double bonds substituted with one or more alkyl groups having from 1 to 4 carbon atoms;

$R_2$ and $R_3$ or $R_1$, $R_2$ and $R_3$ may form, together with the nitrogen atom from which they depend and with at least one other nitrogen, oxygen or sulfur atom, a saturated or unsaturated heterocycle or a saturated or unsaturated heterocycle substituted with one or more alkyl groups having from 1 to 4 carbon atoms;

$R_1$, $R_2$ and $R_3$ may form, together and with the nitrogen atom from which they depend, an unsaturated heterocycle or an unsaturated heterocycle substituted with one or two methyl or ethyl groups; and $R_2$ and $R_3$ or $R_1$, $R_2$ and $R_3$ may form, together with the nitrogen atom from which they depend or together with the nitrogen atom from which they depend and with at least one other nitrogen, oxygen or sulfur atom, a saturated or unsaturated polycyclic compound or a saturated or unsaturated polycyclic compound substituted with one or more alkyl groups having 1 to 4 carbon atoms.

4. The process as defined by claim 3, wherein the amount of said amine present constitute from 0.005% to 10% by weight of the reaction amine.

5. The process as defined by claim 2, said amine catalyst having the general formula (II):

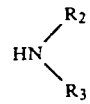

in which
$R_2$ or $R_3$ may be a hydrogen atom; and $R_2$ and $R_3$, which may be identical or different, are each a linear alkyl radical having from 1 to 10 carbon atoms; a secondary alkyl radical having from 3 to 10 carbon atoms; a tertiary alkyl radical having from 4 to 10 carbon atoms; a tertiary alkyl radical having phenyl radical; or a benzyl or phenethyl radical; with the provisos that:

$R_2$ and $R_3$ may form, together with the nitrogen atom from which they depend with at least one of another nitrogen or oxygen atom, a saturated heterocycle or a heterocycle containing one or more olefinic double bonds; and at least one of $R_2$ or $R_3$ may contain one or more amine, hydroxyl or carboxyl acid ester groups.

6. The process as defined by claim 5, wherein said amine catalyst having the general formula (II), at least one of $R_2$ and $R_3$ is a secondary alkyl radical having from 3 to 10 carbon atoms.

7. The process as defined by claim 6, wherein at least one of $R_2$ and $R_3$ is an isopropyl, 2-butyl, 2-pentyl, 3-pentyl, 2-hexyl, 3-hexyl, 2-heptyl, 3-heptyl, 4-heptyl, 2-octyl, 3-octyl, 4-octyl, 2-nonyl, 3-nonyl, 4-nonyl, 5-nonyl, 2-decyl, 3-decyl, 4-decyl, 5-decyl, cyclohexyl or cyclopentyl radical.

8. The process as defined by claim 5, wherein said amine catalyst having the general formula (II), $R_2$ and $R_3$ together form, with the nitrogen atom from which they depend, a 5- or 6-membered heterocycle or a 5- or 6-membered heterocycle containing another nitrogen atom or an oxygen atom.

9. The process as defined by claim 5, wherein said amine catalyst having the general formula (II) comprises n-propylamine, isopropylamine, n-butylamine, isobutylamine, tert-butylamine, n-pentylamine, 2-methylpentylamine, 3-methylpentylamine, 2-ethylhexylamine, laurylamine, cyclohexylamine, cyclopentylamine, benzylamine, glycine ethyl ester, ethanolamine, diisopropylamine, diisobutylamine, dicyclohexylamine, morpholine or imidazole.

10. The process as defined by claim 2, said reaction medium further comprising at least one polychlorophenol, and wherein the ratio by weight of the ortho-chlorophenol/total amount of chlorophenols is no greater than 30%.

11. The process as defined by claim 10, said reaction medium comprising admixture of orthochlorophenol with at least one of 2,6-dichlorophenol, 2,4-dichlorophenol and/or 2,4,6-trichlorophenol.

12. The process as defined by claim 2, comprising (i) conducting the reaction until there exists a concentration of ortho-chlorophenol in the reaction medium of no greater than 30% by weight, and then (ii) continuing the chlorination by simultaneously adding chlorine and ortho-chlorophenol to said reaction medium such as to maintain the concentration by weight therein at a value no greater than 30%.

13. The process as defined by claim 11, wherein said reaction medium further comprises an effective amount of a strong acid or Lewis acid.

14. The process as defined by claim 13, wherein said reaction medium comprises a protonic acid having an acidity function Ho of less than or equal to −5.

15. The process as defined by claim 13, wherein said reaction medium comprises sulfuric acid, perchloric acid, trifluoromethansesulfonic acid, chlorosulfonic acid, fluorosulfonic acid, fuming sulfuric acid or an acidic resin containing fluorosulfonic groups.

16. The process as defined by claim 13, carried out in the presence of aluminum chloride, aluminum bromide, stannic or stannous chloride, stannic or stannous bromide, bismuth trichloride, titanium tetrachloride, zirconium tetrachloride, antimony pentafluoride, tungsten hexachloride, a molybdenum chloride, ferric chloride, ferrous chloride, ferric bromide, ferrous bromide, cuprous chloride, cupric chloride or zinc chloride.

17. The process as defined by claim 16, carried out in the presence of aluminum chloride, ferric chloride, zirconium tetrachloride or titanium tetrachloride.

18. The process as defined by claim 13, wherein the ratio by weight strong acid/dichlorophenol or Lewis acid/dichlorophenol ranges from 0.01% to 10%.

19. The process as defined by claim 2, for the preparation of 2,6-dichlorophenol.

* * * * *